United States Patent
Gracie et al.

(10) Patent No.: US 7,565,286 B2
(45) Date of Patent: Jul. 21, 2009

(54) METHOD FOR RECOVERY OF LOST SPEECH DATA

(75) Inventors: Ken Gracie, Ottawa (CA); John Lodge, Kanata (CA)

(73) Assignee: Her Majesty the Queen in right of Canada, as represented by the Minister of Industry, Through the Communications Research Centre Canada, Ottawa (CA)

( * ) Notice: Subject to any disclaimer, the term of this patent is extended or adjusted under 35 U.S.C. 154(b) by 815 days.

(21) Appl. No.: 10/892,115

(22) Filed: Jul. 16, 2004

(65) Prior Publication Data
US 2005/0015242 A1     Jan. 20, 2005

Related U.S. Application Data

(60) Provisional application No. 60/487,612, filed on Jul. 17, 2003.

(51) Int. Cl.
*G10L 19/00*     (2006.01)
(52) U.S. Cl. .................. 704/217; 704/207; 704/208
(58) Field of Classification Search ............. 704/228, 704/207, 208, 215, 214, 216, 217, 218, 219, 704/226, 220, 200, 205, 209
See application file for complete search history.

(56) References Cited

U.S. PATENT DOCUMENTS

| | | | |
|---|---|---|---|
| 4,052,559 | A | 10/1977 | Paul et al. |
| 5,615,298 | A | 3/1997 | Chen |
| 5,864,795 | A | 1/1999 | Bartkowiak |
| 5,884,010 | A | 3/1999 | Che et al. |
| 6,035,271 | A | 3/2000 | Chen |
| 6,463,407 | B2 | 10/2002 | Das et al. |

(Continued)

OTHER PUBLICATIONS

"A Linear Prediction Based Packet Loss Concealment Algorithm for PCM Coded Speech", Gunduzhan et al, IEEE Trans. On Speech and Audio Processing, vol. 9, No. 8 Nov. 2001, pp. 778-784.

(Continued)

*Primary Examiner*—Huyen X. Vo
(74) *Attorney, Agent, or Firm*—Teitelbaum & Maclean; Neil Teitelbaum; Doug MacLean (57) ABSTRACT

A method for lost speech samples recovery in speech transmission systems is disclosed. The method employs a waveform coder operating on digital speech samples. It exploits the composite model of speech, wherein each speech segment contains both periodic and colored noise components, and separately estimates these two components of the unreliable samples. First, adaptive FIR filters computed from received signal statistics are used to interpolate estimates of the periodic component for the unreliable samples. These FIR filters are inherently stable and typically short, since only strongly correlated elements of the signal corresponding to pitch offset samples are used to compute the estimate. These periodic estimates are also computed for sample times corresponding to reliable samples adjacent to the unreliable sample interval. The differences between these reliable samples and the corresponding periodic estimates are considered as samples of the noise component. These samples, computed both before and after the unreliable sample interval, are extrapolated into the time slot of the unreliable samples with linear prediction techniques. Corresponding periodic and colored noise estimates are then summed. All required statistics and quantities are computed at the receiver, eliminating any need for special processing at the transmitter. Gaps of significant duration, e.g., in the tens of milliseconds, can be effectively compensated.

19 Claims, 7 Drawing Sheets

U.S. PATENT DOCUMENTS 6,549,886 B1    4/2003   Partalo
7,143,032 B2 *  11/2006  Chen ........................ 704/228

OTHER PUBLICATIONS

"A New Hybrid Long-Term and Short-Term Prediction Algorithm for Packet Loss Erasure over IP-Networks" International Symposium on Signal Processing and its Applications, ISSPA 2003.

"A Survey of Error-Concealment Schemes for Real-Time Audio and Video Transmissions over the Internet", Wah et al, IEEE 2000 pp. 17-24.

"Real-Time Implementation of Time Domain Harmonic Scaling of Speech for Rate Modification and Coding", Cox et al, IEEE Journal of Solid-State Circuits, vol. SC-18, No. 1, Feb. 1983.

"The Effect of Waveform Substitution of the Quality of PCM Packet Communications", Wasem et al, IEEE Transactions on Acoustics, Speech and Signal Processing, vol. 36, No. 3 Mar. 1988, pp. 342-348.

"Effects of Packet Losses in Waveform Coded Speech and Improvements due to an Odd-Even Sample Interpolation Procedure", Jayant et al, IEEE Transactions on Communications, vol. 29, No. 2, Feb. 1981, pp. 101-109.

"Model-Based Multirate Representation of Speech Signals and Its Application to Recovery of Missing Speech Packets", Chen et al. IEEE Transactions on Speech and Audio Processing, vol. 5, No. 3, May 1997, pp. 220-230.

"Applying the Harmonic Plus Noise Model in Concatenative Speech Analysis", Stylianou, IEEE Transactions on Speech and Audio Processing, vol. 9, No. 1, Jan. 2001, pp. 21-29.

"Digital Signal Processing" Principles, Algorithms, and Applications, Proakis et al, Prentice Hall, $3^{rd}$ Ed, 1996, pp. 852-906 and pp. 531-539.

"Discrete-Time Processing of Speech Signals", Deller et al, IEEE Press/Wiley-Interscience, 1993.

"Linear Prediction: A Tutorial Review", Makhoul, IEEE vol. 66, pp. 58-77, Apr. 1975 (Invited Paper).

\* cited by examiner

METHOD FOR RECOVERY OF LOST SPEECH DATA

CROSS-REFERENCE TO RELATED APPLICATIONS

This application claims priority of U.S. Provisional Patent Application No.: 60/487,612 filed Jul. 17, 2003, entitled "Thick Volume Hologram for Microwave Frequency Band and Estimation of Unreliable Digital Speech Samples via Composite Modelling and Adaptive Filtering", which is incorporated herein by reference for all purposes.

FIELD OF THE INVENTION

This invention relates to the field of digital communications and speech transmission in wireline and wireless systems. More particularly, the invention relates to a method for recovery of lost or corrupted segments of waveform coded speech signals using time-domain interpolation and statistical properties of the speech signal.

BACKGROUND OF THE INVENTION

In a communication system, signals may be periodically lost or corrupted in many ways. Examples include a loss or long delay of packets in a packet-switched system, a loss or corruption of sample sequences due to slow hardware response in a frequency-hopped system and a loss or corruption of sample sequences due to a poor wireless channel. All such cases introduce intervals into the signal wherein the signal is either unreliable or completely unavailable. These gaps or erasures occur in both wire-line and wireless systems.

With a voice signal, these gaps or erasures degrade the perceived quality of the speech content. This degradation can significantly interfere with the listener's ability to understand the content of the signal and could mean that the communications link is effectively unusable. Even assuming that the content is intelligible, such gaps reduce the usefulness of the link by irritating the listener. Therefore, the mitigation of this phenomenon is of significant importance in attempting to deliver voice services at an acceptable level of quality.

Fortunately, speech signals themselves provide useful tools for overcoming this kind of degradation. Speech may be modeled as a response of a slowly, time-varying, linear system representing the vocal tract to either quasi-periodic or noise-like inputs. Quasi-periodic input refers to an excitation with a line spectrum whose fundamental, i.e., pitch frequency varies with time and corresponds to voiced sounds, e.g. 'e' or 'a' sounds, produced by the vocal cords. Noise-like input refers to a signal resulting from turbulence in the vocal tract, e.g. 's' or 'f' sounds. Voiced sounds typically dominate speech sequences, both in terms of time and energy. The linear system modulates the excitation, displaying resonance or formant frequencies that vary over time. This model may be further simplified by examining the speech signal on a short-time basis, where "short-time" implies bursts of a few tens of milliseconds in duration. Over such intervals, the periodic excitation may be viewed as stationary and the vocal tract impulse response as time-invariant.

Communication systems for transmitting speech signals fall into one of two categories: those using parametric coding and those tint use waveform coding. Mitigation of lost or corrupted signal segments for parametric coded systems is a distinct problem that has been extensively addressed, primarily in a context of linear prediction coding, and many solutions to this problem have been disclosed in prior art. In the context of waveform coding systems, which relate directly to this invention, a variety of approaches to compensating or restoring speech signals suffering from such erasures or losses have been proposed. For example, O. J. Wasem, D. J. Goodman, C. A. Dvorak and II. G. Page, in an article entitled "The Effect of waveform substitution on the quality of PCM packet communications", IEEE Transactions on Speech and Audio Processing, Vol. 36, No. 3, March 1988, pp. 342-348, and M. Partalo, in "System For Lost Packet Recovery in Voice over Internet Protocol Based on Time Domain Interpolation". U.S. Pat. No. 6,549,886, disclose methods based on waveform substitution wherein copies of reliable sample sequences are inserted into intervals corresponding to unreliable samples. These methods may repeat sequences whose length is equal to a pitch period. Other variations of this method perform time-domain correlations in an attempt to find a sequence equal in duration to a set of unreliable samples. Weighting or scaling functions are often applied to the samples in order to smooth transitions between reliable and unreliable intervals. These techniques typically ignore or make only limited use of statistical properties of speech and often use only preceding samples in forming their estimates.

Methods based on linear prediction (LP) are widespread and well documented; the interested reader is referred to a paper by E. Gunduzhan and K. Momtahan, entitled "A linear prediction based packet loss concealment algorithm for PCM coded speech", IEEE Transactions on Speech and Audio Processing, Vol. 9, No. 8, November 2001, pp. 778-784, and J. -H. Chen, "Excitation signal synthesis during frame erasure or packet loss", U.S. Pat. No. 5,615,298. These methods compute statistical model parameters for a transmitted speech signal assuming that it is an autoregressive (AR) process, i.e., a weighted sum of past outputs plus an excitation term. These AR models are necessarily always represented as infinite impulse response (IIR) systems. These techniques must be carefully designed to ensure stability and only utilize prior data in computing estimates of the unreliable samples.

Methods based on sample interpolation generate estimates of unreliable samples from adjacent reliable samples, as disclosed for example in N. S. Jayant and S. W. Christensen, "Effects of packet losses in waveform coded speech and improvements due to an odd-even sample-interpolation procedure", IEEE Transactions on Communications, Vol. 29, No. 2, February 1981, pp. 101-109, and Y. -L. Chen and B. -S. Chen, "Model-Based Multirate Representation of Speech Signals and Its Application to Recovery of Missing Speech Packets", IEEE Transactions on Speech and Audio Processing, Vol. 5, No. 3, May 1997, pp. 220-230. These methods often rely on interleaving the speech data samples at the transmitter and attempt to ensure that unreliable samples are interspersed with reliable samples at the receiver. Linear optimum, i.e., Wiener or Kalman, filtering techniques are used to generate the interpolation filters, and statistical parameters required to generate them may be computed at the receiver or sent from the transmitter.

All of the aforementioned techniques have their strengths and weaknesses. Although they appear to perform their intended functions, none of them provides a method for lost sample recovery or compensation that simultaneously: a) makes effective use of the statistics of the speech signal while remaining practical from a computational standpoint, b) uses only reliable samples that are highly correlated with the unreliable samples and separated from them in time by pitch offsets, c) incorporates reliable data from both sides of an unreliable sequence, d) generates an interpolation filter with no stability concerns and e) requires no pre-processing or transmitting of additional information from the transmitter.

In particular, most of heretofore disclosed methods for recovery of lost or corrupted segments of speech data either do not analyse and use statistical information present in the received speech data, or use it in a limited and simplified way. For example, a lost segment of speech is typically considered to contain either a voiced quasi-periodic signal, or a noise-like signal. However, preserving a stochastic component of the sound, i.e. the information concerning the "stochastic evolution" of the timbre and the added noises as breath etc., is very important for maintaining perceived sound quality. Recently, such composite, or "harmonic plus noise" models of speech attempting to address this problem have been developed for speech coding; For example Y. Stylianou discloses such a model in a paper entitled, "Applying the Harmonic Plus Noise Model in Concatenative Speech Analysis", *IEEE Transactions on Speech and Audio Processing*, Vol. 9, No. 1, January 2001, pp. 21-29, and U.S. Pat. No. 6,741,960 to Kim, et al. To the best of the inventors' knowledge, however, no methods for lost speech samples recovery in waveform-coded transmission systems attempting to recover both quasi-periodic and noise-like component for all lost speech samples has been disclosed heretofore.

An object of this invention is to provide a method of estimation of both quasi-periodic and noise components of lost segments of digitized wave-form coded speech.

Another object of this invention is to provide a method for receiver-based recovery of lost segments of speech or sound data in a speech transmitting system using time-domain adaptive interpolation, linear prediction and statistical analysis of the received speech data.

In accordance with this invention a waveform coder operating on uncompressed PCM speech samples is disclosed. It exploits the composite model of speech, i.e. a model wherein each speech segment contains both periodic and colored noise components, in order to separately estimate the different components of the unreliable samples.

First, adaptive finite impulse response (FIR) filters computed from received signal statistics are used to interpolate estimates of the periodic component for the unreliable samples. These FIR filters are inherently stable and also typically very short, since only strongly correlated elements of the signal corresponding to pitch offset samples are used to compute the estimate. One embodiment uses a filter of length 1. These periodic estimates are also computed for sample times corresponding to reliable samples adjacent to the unreliable sample interval. The differences between these reliable samples and the corresponding periodic estimates are taken to be samples of the noise component. These samples, computed both before and after the unreliable sample interval, are extrapolated into the time slot of the unreliable samples with linear prediction techniques. Corresponding periodic and colored noise estimates are then summed. All required statistics and quantities are computed at the receiver, eliminating any need for special processing at the transmitter. Gaps of significant duration, e.g., in the tens of milliseconds, can be effectively compensated.

SUMMARY OF THE INVENTION

In accordance with the invention, a method for recovering lost speech samples in a speech transmission system is provided comprising the steps of: a) receiving a composite sequence of speech samples which includes a sequence of unreliable speech samples and a sequence of reliable speech samples, each speech sample having a value and a position in the composite speech sequence, the composite sequence of speech samples having a pitch period $T_p$ having a value between a minimum value $T_{min}$ and a maximum value $T_{max}$; b) identifying a set of time lags from correlations between at least some of the reliable speech samples by performing the steps of i) computing a set of autocorrelation coefficients for the sequence of reliable speech samples for a sequence of time lags, ii) identifying a subset of largest autocorrelation coefficients from the set of correlation coefficients corresponding to time lags between $T_{min}$ and $T_{max}$, iii) identifying a set of time lags corresponding to the subset of largest autocorrelation coefficients; c) selecting a first subset of speech samples from the composite sequence of speech samples including at least some of the unreliable speech samples; d) for a speech sample from the first subset of speech samples, selecting a set of reliable speech samples wherein each reliable speech sample is offset from the speech sample from the composite sequence of speech samples by a time lag from the set of time lags; e) computing a periodic estimate for the speech sample from the first subset of speech samples using the set of reliable speech samples and using an adaptive FIR interpolation filter, wherein the adaptive FIR interpolation filter is dependent on a position of the speech sample from the first subset of speech samples; f) repeating steps (d) and (e) for each speech sample from the first subset of speech samples.

In one embodiment, the sequence of reliable speech samples includes a first sequence of reliable speech samples preceding the sequence of unreliable speech samples and a second sequence of reliable speech samples following the sequence of unreliable speech samples; and, the step of selecting a set of reliable speech samples for a speech sample from the first subset of speech samples comprises the steps of: identifying a local subset of M time lags of the set of time lags from time offsets between the speech sample and the set of reliable speech samples, and identifying a local subset of autocorrelation coefficients corresponding to the local subset of time lags.

The tap coefficients of the FIR interpolation filter can be determined by performing the steps of: constructing an M×M autocorrelation matrix from a set of correlation coefficients corresponding to differences between time lags from the local subset of M time lags, inverting the autocorrelation matrix to obtain an inverted autocorrelation matrix, multiplying the inverted autocorrelation matrix by a vector formed from the local subset of correlation coefficients for obtaining a vector of the tap coefficients.

In another embodiment, the FIR interpolation filter for each sample position from the first subset of speech samples has a length of 1, and the tap coefficient is determined by a largest autocorrelation coefficient from the local subset of autocorrelation coefficients corresponding to a reliable sample.

In accordance with another aspect of this invention, the first subset of speech samples comprises an overlap set of reliable speech samples adjacent to the sequence of unreliable speech samples, and the method for recovering of lost speech samples further comprises the steps of: a) obtaining a set of difference samples by computing a difference between speech samples from the overlap set of reliable speech samples and the periodic estimates for corresponding speech samples from the overlap set of speech samples, and b) for each unreliable speech sample, performing the steps of i) obtaining an estimate of a colored noise component of the unreliable speech sample by extrapolating the set of difference samples to the unreliable speech sample position using autoregressive filtering of the difference samples and white Gaussian noise excitation, and ii) combining the previously computed periodic estimate of the unreliable speech sample and the estimate of the colored noise component of the unreliable speech sample for determining an estimate of a value of the unreliable speech sample.

The overlap set can include a first overlap set preceding the sequence of the unreliable speech samples and a second overlap set following the sequence of the unreliable speech samples, in which case the step of obtaining the estimate of the colored noise component for an unreliable speech sample is performed by combining two colored noise estimates for the unreliable speech sample computed using autoregressive filtering of first and second sets of difference samples corresponding to the first and second overlap sets of reliable speech samples.

BRIEF DESCRIPTION OF THE DRAWINGS

Exemplary embodiments of the invention will now be described in conjunction with the drawings in which.

DETAILED DESCRIPTION OF THE PREFERRED EMBODIMENT

Several definitions and notations used hereafter will be now described.

A term "speech sample" is used in this specification to mean a data sample obtained by sampling an analog signal representing speech at a pre-determined sampling rate; a speech sample can have a complex or a real value.

Words "an estimate of a speech sample" or simply "an estimate of a sample" are used in this specification to mean an estimate of a value of the speech sample.

A term "periodic component" for a speech sample from a sequence of speech samples is used in this specification to mean a component of the speech sample corresponding to a voiced component of the sequence of speech samples, said voiced component being quasi-periodic and having a pitch period or several pitch periods.

A term "noise component" for a speech sample from a sequence of speech samples is used in this specification to mean a component of the speech sample corresponding to a un-voiced component of the sequence of speech samples, said un-voiced component having characteristics of a modulated stochastic signal, or colored noise.

The term quasi-periodic in relation to a time-ordered sequence of speech data samples is used in this specification to mean a sequence of data having a time period or a set of time periods that can vary in time.

A term "periodic estimate" is used in this specification to mean an estimate of a periodic component of a speech sample from a sequence of speech samples.

A term "noise estimate" is used in this specification to mean an estimate of a noise component of a speech sample from a sequence of speech samples.

Exemplary embodiments of a method for recovery of lost speech samples is shown in FIGS. 2-7 and are hereafter described.

Figure 1A:
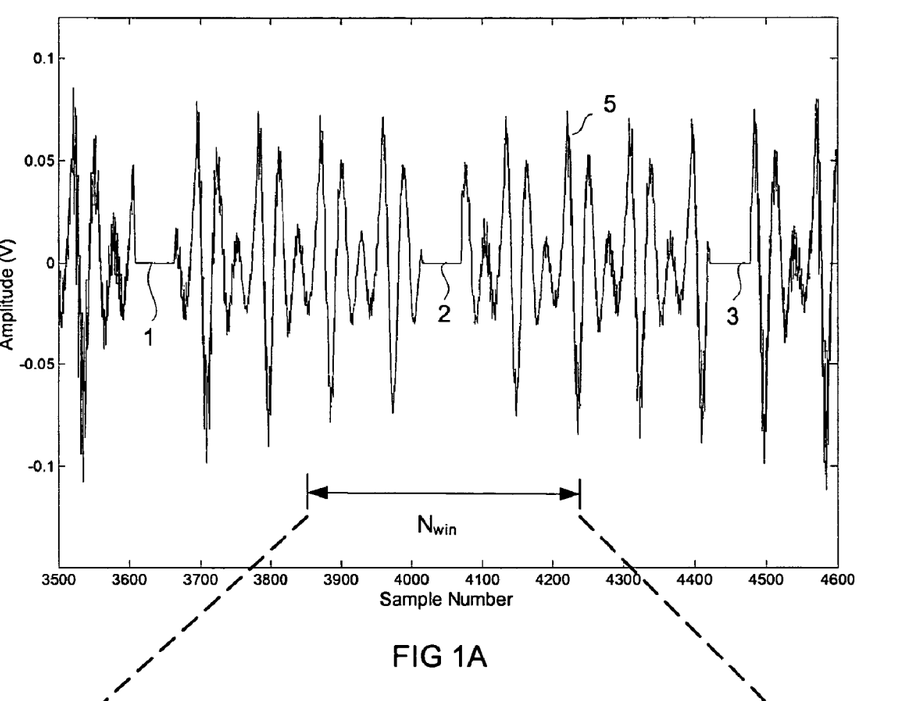
FIG. 1A is an exemplary plot of a received sequence of speech samples.

With reference to FIG. 1A, a received sequence 5 of digital speech samples in a transmission system employing digital waveform coding may include multiple sequences 1, 2, 3 of lost, delayed or otherwise corrupted speech samples; these speech samples which have values not known with sufficient certainty at the time of processing are referred hereafter as lost or unreliable speech samples. The samples are separated in time by a sampling period $T_s=1/f_s$, wherein $f_s$ is a sampling frequency. A normalized time delay $l=T_l f_s$ between two samples separated by l sampling periods, where $T_l$ is a non-normalized time interval therebetween, is hereafter referred to as a time lag, or a correlation lag.

In an exemplary embodiment described herein the speech samples are assumed to have real values.

The received sequence of speech samples 5 in general case has a voiced component and a noise-like component; in some cases one of those components can prevail The voiced component has a pitch period $T_p$ and a corresponding pitch frequency $f_p=1/T_p$ that can be changing during the speech sequence, but is expected to be between a minimum pitch frequency $f_{min}=1/T_{max}$ and a maximum pitch frequency $f_{max}=1/T_{min}$, wherein the $T_{min}$ and $T_{max}$ are corresponding minimum and maximum pitch periods determined by known properties of voiced speech. The voiced component is hereafter referred to also as a periodic component or a quasi-periodic component. Other pitch frequencies between $f_{min}$ and $f_{max}$ and can be present in a spectrum of the voiced component. The noise-like component of the composite speech sequence, which can result from turbulences in the vocal tract, is viewed as a modulated, or correlated, noise, and is referred to hereafter as a colored noise component or simply as a noise component of a speech sample sequence.

The present invention provides a method for estimating both a noise component and a periodic component for each missing or unreliable speech sample; the results of these estimates will be referred to respectively as noise and periodic estimates of a speech sample, or simply as to a noise estimate and a periodic estimate.

Figure 1B:
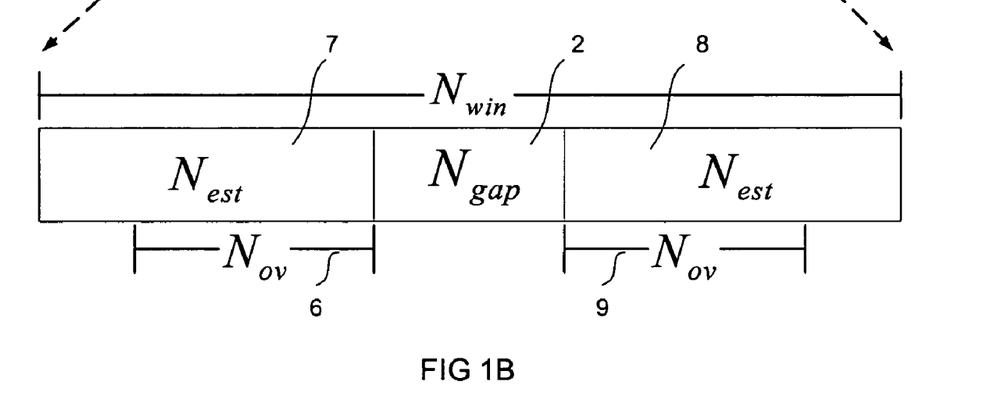
FIG. 1B is a diagram of a composite sequence of speech sample.
Figure 2:
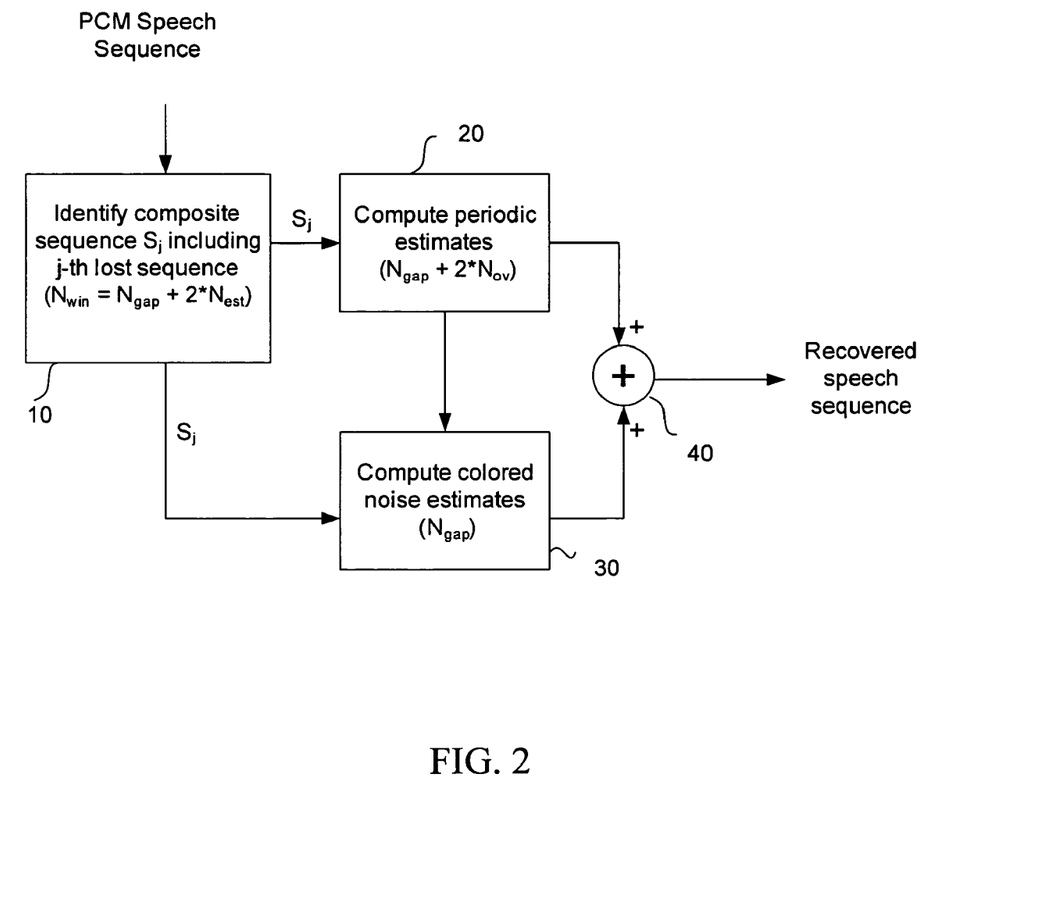
FIG. 2 is a general diagram of a method for lost speech samples recovery according to instant invention.

FIG. 2 presents a top-level view of an exemplarity embodiment of the method of present invention. In a first step 10, for each sequence of lost speech samples from a received sequence 5 of speech samples, a symmetrical ordered sequence of $N_{win}$ speech samples including the sequence of lost speech samples is identified; this speech sequence is hereafter referred to as a composite sequence of speech samples. With reference to FIG. 1B, the composite sequence of speech samples consists of the sequence '2' of $N_{gap}$ unreliable samples, and a non-contiguous sequence 7,8, of $2 \cdot N_{est}$ reliable speech samples surrounding the sequence 2 of $N_{gap}$ unreliable samples, so that $N_{win}$ equals $2 \cdot N_{est}+N_{gap}$. The non-contiguous sequence 7,8 of reliable samples consists of a first sequence 7 of $N_{est}$ reliable samples immediately preceding the sequence of unreliable samples, and a second sequence 8 of $N_{est}$ reliable samples immediately following the sequence of unreliable samples.

In an illustrative embodiment considered herein, $N_{est} \geq 2 M_{max}$, where $M_{max}$, defined hereafter by relation (2), is a time lag corresponding to the maximum pitch period. In other embodiments, the composite sequence of speech samples can be asymmetric, with the first and second sequences of reliable samples containing differing number of speech samples, with either of these sequences containing less than $2M_{max}$ samples.

In a next general step 20, periodic estimates for the unreliable speech samples are identified from the first 7 and second 8 sequences of reliable speech data using time-domain interpolation by FIR filtering. If noise estimates for the unreliable speech samples are to be computed as well, the periodic estimates are generated also for overlap sets 6 and 9 of reliable speech samples adjacent to the unreliable speech sample both before and after thereof, as shown in FIG. 1B.

In a next general step 30, a set of Ngap colored noise estimates is computed by extrapolating a noise component extracted from the reliable speech samples from the overlap sets 6,9 using the periodic estimates for speech samples from the overlap sets 6,9.

In a final step 40, the periodic estimates and the noise estimates are added together to provide estimates for the $N_{gap}$ unreliable samples from the sequence 2 of unreliable speech samples.

The general steps 20 and 30 wherein the periodic estimates and the noise estimates are generated will now be described in further detail.

First, a method for generation of estimates of the voiced component of the speech signal, or the periodic estimates, is described for two illustrative embodiments. The generation of estimates of the noise-like component of the speech signal, or the coloured noise estimates, is then described in relation to the periodic estimation process.

Hereforth values of the unreliable set of samples will be assumed to be set to zeros.

Figure 3:
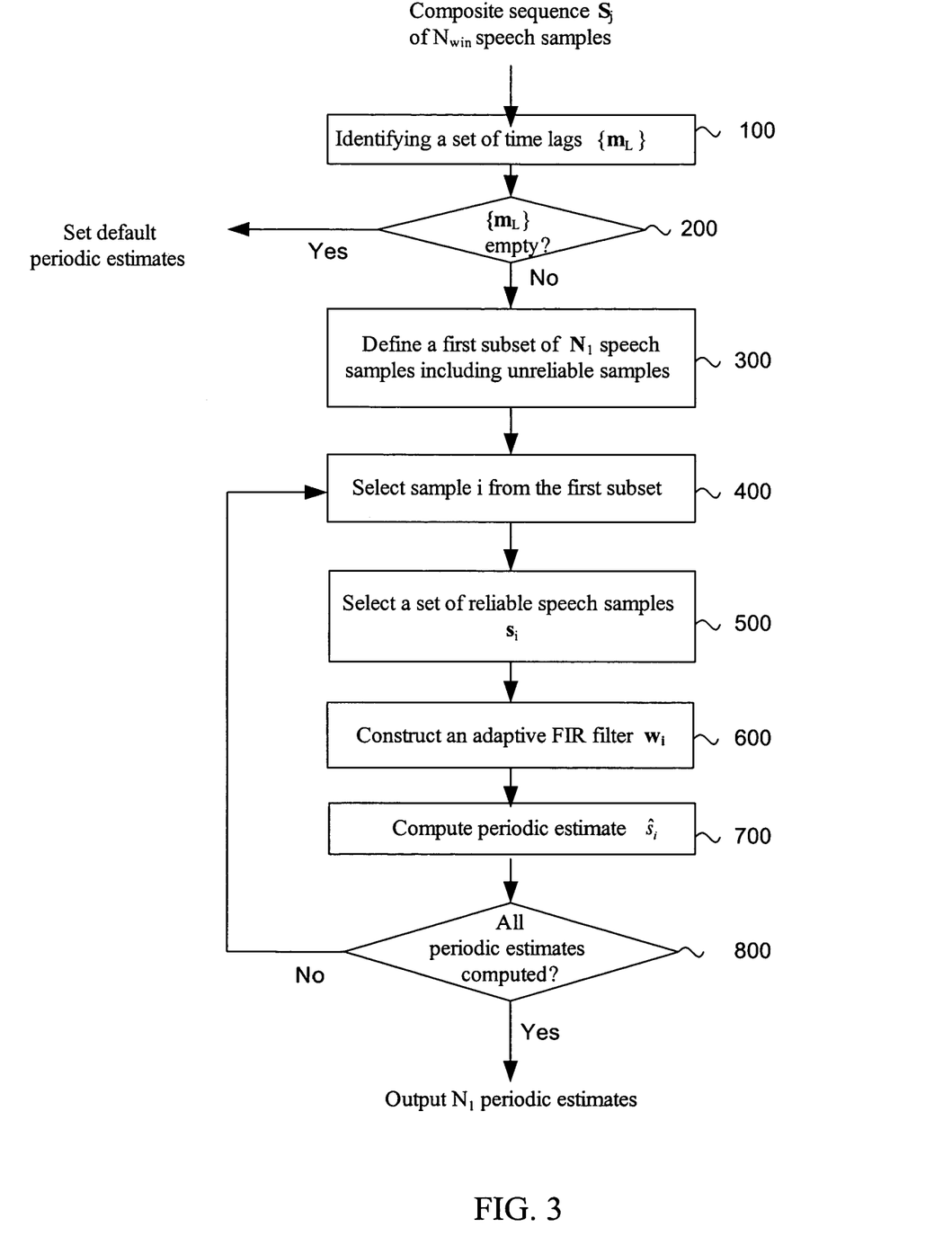
FIG. 3 is a diagram of a general method for generation of periodic estimates according to instant invention.

Generation of the periodic estimates in accordance with a first illustrative embodiment will now be described with reference to FIG. 3.

Figure 4:
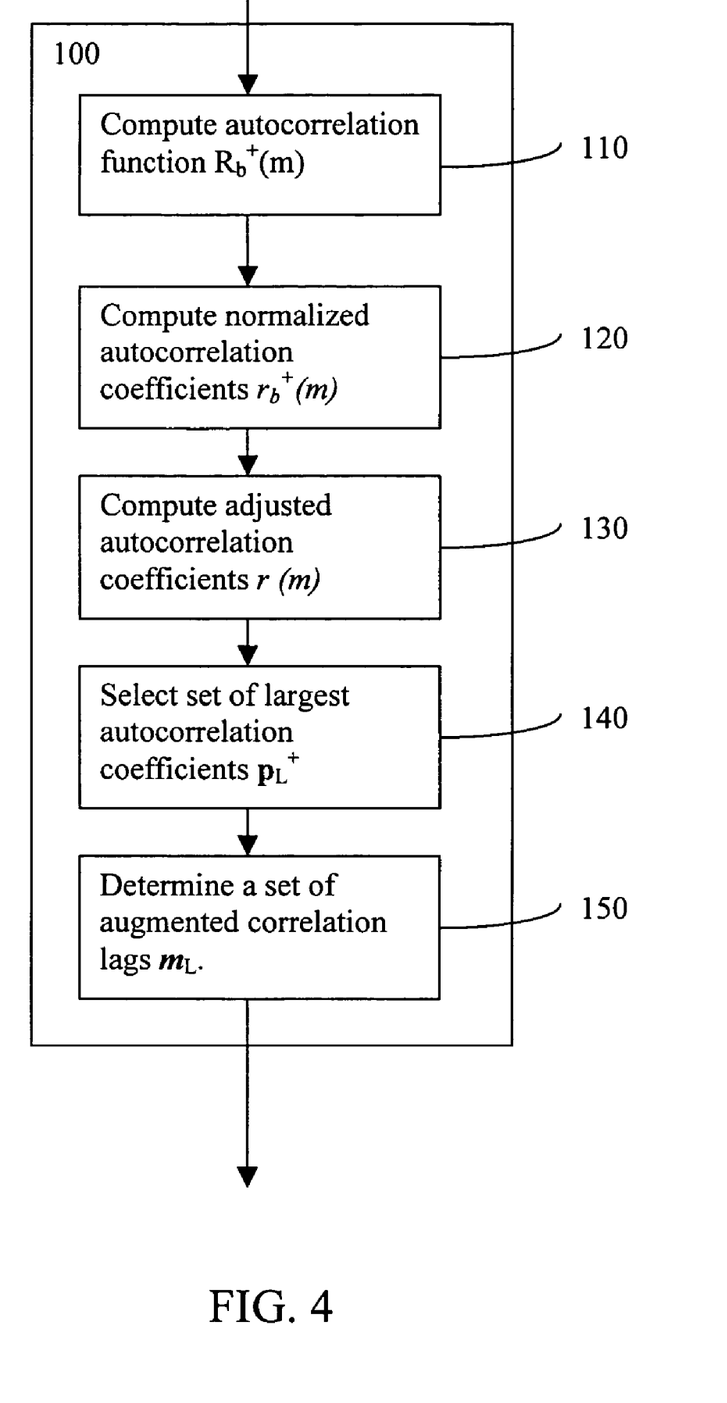
FIG. 4 is a diagram of a process of identifying a set of time lags for the method of FIG. 3.

In a first step 100, a $j^{th}$ composite sequence $S_j$ of speech samples $s_j(n)$, where n is an integer denoting a position of the sample in the composite sequence of speech samples, is selected from the received speech sequence, and a set of time lags corresponding to pitch periods which are likely to be present in the $j^{th}$ composite sequence of speech samples is identified. This step further includes steps 110-150 which will be described with reference to FIG. 4. First, in a step 110, an autocorrelation function $R_b^+(m)$ for the $j^{th}$ composite sequence $S_j$ is computed for all time lags $T_m = m \cdot T_s$ between 0 and $2 \cdot T_{max} = 2 \cdot M_{max} T_s$ in accordance with a formula $$R_b^+(m) = w(m) \cdot \sum_{l=|m|}^{N_{win}-|m|} s_j^*(l) \cdot s_j(l-m), m = 0, \ldots, 2 \cdot M_{max}, \quad (1)$$

where m is a unit-less correlation lag hereafter referred to simply as a correlation lag, and $$M_{max} = \left\lfloor \frac{f_s}{f_{min}} \right\rfloor \quad (2)$$

is a lag corresponding to the lowest pitch frequency of interest $f_{min}$, and w(m) is an appropriate normalization function. This correlation calculation is only done over the set of reliable samples, and only those values corresponding to positive lags must be explicitly computed since the autocorrelation function (1) is guaranteed to be conjugate-symmetric. The normalization function w(m) may take on a plurality of different values. As those skilled in the art will realize, one possibility is to use an unbiased autocorrelation normalization, wherein 1/w(m) is set to be equal to a number of non-zero terms in the summation in the right-hand side of formula (1):

$$w(m) = \begin{cases} \frac{1}{N_{win} - 2 \cdot |m| - N_{gap}}, & 0 \leq |m| < N_{gap} \\ \frac{1}{N_{win} - |m| - 2 \cdot N_{gap}}, & N_{gap} \leq |m| < N_{est} \\ \frac{1}{N_{win} + |m| - 2 \cdot N_{gap}}, & N_{est} \leq |m| < N_{est} + N_{gap} \\ \frac{1}{N_{win} - |m|}, & N_{est} + N_{gap} \leq |m| < N_{win}. \end{cases} \quad (3)$$

This version of w(m) assumes $N_{est} \geq N_{gap}$; a similar expression applies when $N_{est} \leq N_{gap}$, but with positions of these two variables in (3) interchanged. An unbiased form of a time-average autocorrelation function is appropriate since it yields an unbiased estimate of an ensemble autocorrelation function for finite data sets, as described for example by J. G. Proakis and D. G. Manolakis, in "Digital Signal Processing: Principles, Algorithms, and Applications", Prentice Hall, $3^{rd}$ Edition, 1996. In addition, a linear rather than a circular correlation is appropriate for this problem because the analysis window is not continuous in a modulo sense.

In a next step 120, a set of $(2 \cdot M_{max}+1)$ correlation coefficients $r_b^+(m)$ are then calculated from the autocorrelation function (1) using a formula (4):

$$r_b^+(m) = \frac{R_b^+(m)}{R_b^+(0)}, m = 0, \ldots, 2 \cdot M_{max}. \quad (4)$$

Since a significant number of samples are unreliable and therefore cannot contribute to the correlation sum in (1), the autocorrelation function $R_b$ and the corresponding correlation coefficients $r_b^+(m)$ may need to be adjusted in order to guarantee that $R_b$ is positive definite and therefore a legitimate autocorrelation function. This adjustment may take many forms; a preferred approach is to force a spectrum of the autocorrelation function to be positive. That is, a new adjusted set of autocorrelations R(m) is calculated in a next step 130 that satisfies an expression $$S(u) = \begin{cases} Re\{S_b(u)\}, & Re\{S_b(u)\} \geq \varepsilon \\ \varepsilon, & Re\{S_b(u)\} < \varepsilon \end{cases}$$

where $$R_b(m) \xleftrightarrow{F} S_b(u)$$

and $$R(m) \xleftrightarrow{F} S(u)$$

are discrete Fourier transform (DFT) pairs, and $\varepsilon$ is a small positive constant which is greater than zero; for example, it can be set to any number between zero and 1% of a maximum magnitude of $S_b(u)$. This operation produces a correlation function $R(m)$ that is closely related to the original function $R_b(m)$ but is guaranteed to be positive definite. If $R_b(m)$ is already positive definite then this operation has no effect except that the minimum spectral sample is forced to be $\epsilon$. Adjusted correlation coefficients for non-negative lags are denoted by $r(m)$.

Once the adjusted correlation coefficients $r(m)$ have been computed, in a next step 140 a set $p_L^+$ of largest adjusted correlation coefficients is selected from the adjusted correlation coefficients corresponding to lags from an interval $m_I^+ = [M_{min}, M_{max}]$ where $$M_{min} = \left\lfloor \frac{f_s}{f_{max}} \right\rfloor \quad (5)$$

is a lag corresponding to the highest pitch frequency of interest $f_{max}$. A corresponding set of time lags $m_L^+$ is determined, and vectors $$m_L^+ = m_I^+|_{|r(m_I^+)| \geq T_{corr}} = [m_1 m_2 \ldots m_L]^T \quad (6)$$

and $$p_L^+ = [r(m_1) \, r(m_2) \ldots r(m_L)]^T \quad (7)$$

are formed from these sets. In one embodiment, L is a number of adjusted correlation coefficients that meet or exceed a predefined threshold $T_{corr}$, $|r(m)| \geq T_{corr}$. In other embodiments, L can be a number of adjusted correlation coefficients having either an imaginary part or a real part, or a magnitude of the imaginary part or of the real part exceeding a pre-determined threshold.

In another embodiment, L can be a fixed pre-determined number, and the vectors (6) and (7) are determined by selecting a set of top L largest correlation coefficients.

Elements of vectors $m_L^+$ and $p_L^+$ are hereafter referred to as surviving coefficients and surviving coefficient lags, respectively.

Since it is desirable to utilize all available reliable samples both preceding and following the unreliable samples, in a next step 150 these vectors are then augmented to include corresponding terms for negative lags, and vectors $$m_L = [-m_L \ldots -m_1 \, m_1 \ldots m_L]^T \quad (8)$$

and $$p_L = [r^*(m_L) \ldots r^*(m_1) \, r(m_1) \ldots r(m_L)]^T \quad (9)$$

are constructed, where the fact that the autocorrelation function is conjugate-symmetric is exploited. The vector $p_L$ is hereafter referred to as a set of augmented surviving coefficients and the vector $m_L$ as a set of augmented surviving coefficient lags.

If the set of augmented surviving coefficients $p_L$ or the corresponding set of time lags $m_L$ is empty, processing of the current burst of speech samples stops, and a vector of periodic estimates for the unreliable speech samples is created with elements set equal to a predefined global default value, e.g. zero or low-level colored noise. If the set of augmented surviving coefficients and the corresponding set of time lags are not empty, the algorithm proceeds to generate a set of periodic estimates based upon these sets.

In a next step 300, a subset of $N_1$ speech samples for which the periodic estimates are to be determined is identified; this subset is hereafter referred to as a first subset of speech samples. In a preferred embodiment, the first subset of speech samples is composed of the sequence of unreliable speech samples and an overlap set of speech samples from the sequence of reliable speech samples adjacent hereto, wherein the overlap set of speech samples is composed of $N_{ov}$ reliable speech samples 6 immediately before the sequence of the unreliable speech samples 2, hereafter referred to as a first overlap set of speech samples, and $N_{ov}$ reliable speech samples 9 immediately following the sequence of unreliable speech samples 2, hereafter referred to as a second overlap set of speech samples, as shown in FIG. 1A, so that $N_1 = N_{gap} + 2N_{ov}$.

In other embodiments, the first subset of speech samples for which the periodic estimates are to be determined can include only some of the unreliable speech samples and/or only some of the preceding or following reliable samples, wherein estimates for other unreliable samples not included in the first subset could be obtained using alternative methods, for example by interpolating periodic estimates obtained for the first subset of speech samples. In other embodiments, the first subset can consist of only some or all of the unreliable speech samples and do not include reliable speech samples.

In a next step 400, a sample position i from the first subset of speech samples is selected, and the processing proceeds to determine a periodic estimate for this sample. In a step 500, a set of reliable speech samples $s_i$ for this sample is selected, wherein each said reliable speech sample is offset from the speech sample by a time lag from the set of time lags $m_L$. First, for each sample position i from the first subset of speech samples, a local subset $m_i$ of lags $$m_i = [m_{i,1} \, m_{i,2} \ldots m_{i,M}]^T \quad (10)$$

is determined which includes all lags m from the set of time lags $m_L$ for which a sum $(m+i)$ yields a sample position for a reliable sample from the current burst. If this is true for a given lag m, then a reliable speech sample $s(i-m)$ is available at the offset m, and both this sample $s(i-m)$ and a corresponding correlation coefficient $r(m)$ are retained; otherwise they are deleted. In expression (10) M is a total number of lags retained, $M \leq L$, and the elements of $m_i$ may be either positive or negative.

Knowing the local subset of lags, a corresponding local subset of correlation coefficients $p_i$, $$p_i = [r(m_{i,1}) \, r(m_{i,2}) \ldots r(m_{i,M})]^T, \quad (11)$$

and the set of reliable samples $s_i$:

$$s_i = [s_j(i-m_{i,1}) \, s_j(i-m_{i,2}) \ldots s_j(i-m_{i,M})]^T \quad (12)$$

are found for each sample position i from the first subset. Elements of $p_L$ ($m_L$) are referred to as useful coefficients (useful coefficient lags) for sample index i.

Note that the samples from the set of speech samples $s_i$ are taken from the original known data, not from a process corresponding to the adjusted correlations. If $s_i$ is empty, the $i^{th}$ periodic estimate is set to the global default value and processing for sample time i is complete.

In a next step 600, a Finite Impulse Response (FIR) filter is constructed for each sample position i from the first subset of speech samples. If $s_i$ is not empty, an autocorrelation matrix $R_i$ is constructed from a set of correlation coefficients corresponding to differences between time lags from the local subset of M time lags:

$$R_i = \begin{bmatrix} r(m_{i,1} - m_{i,1}) & r(m_{i,1} - m_{i,2}) & \ldots & r(m_{i,1} - m_{i,M}) \\ r(m_{i,2} - m_{i,1}) & r(m_{i,2} - m_{i,2}) & & \\ \vdots & & \ddots & \vdots \\ r(m_{i,M} - m_{i,1}) & & \ldots & r(m_{i,M} - m_{i,M}) \end{bmatrix} \quad (13)$$

-continued $$= \begin{bmatrix} r(0) & r^*(m_{i,2} - m_{i,1}) & \cdots & r^*(m_{i,M} - m_{i,1}) \\ r(m_{i,2} - m_{i,1}) & r(0) & & \vdots \\ \vdots & & \ddots & \vdots \\ r(m_{i,M} - m_{i,1}) & & \cdots & r(0) \end{bmatrix}$$

where δ is a constant. The last equality in (13) once again makes use of the fact that the autocorrelation function is conjugate-symmetric. The computation of lag differences in expression (13) is the reason for computing $2 \cdot M_{max}$ rather than $M_{max}$ autocorrelations in (1). In a worst case, lags of both $M_{max}$ and $-M_{max}$ may be included in the useful coefficients, resulting in a term $r(2 \cdot M_{max})$ appearing in (24). This is also the reason for computing correlations at lags below $M_{min}$, since small lag differences can also arise when computing the autocorrelation matrix (13), for example $M_{max} - (M_{max} - 1) = 1$.

In a next step 600, a vector $w_i$ of tap coefficients of a FIR interpolation filter, known in the art as a Wiener filter, is then computed for sample index i as $$w_i = R_i^{-1} \cdot p_i \quad (14)$$

and, in a step 700 the $i^{th}$ periodic estimate $\hat{s}_i$ is computed as $$\hat{s}_i = w_i^T \cdot s_i \quad (15)$$

The steps 500, 600 and 700 are repeated for all speech samples from the first subset of speech samples until $N_1$ periodic estimates are determined, forming a vector of periodic estimates $\hat{s}_P(n)$. Note that in some embodiments these steps can also be performed in parallel for all $N_1$ samples, for example in a sequence of matrix operations.

This completes the step 20 of estimating the periodic components and generating the periodic estimates for the sequence of unreliable speech samples in the exemplary embodiment.

Figure 5:
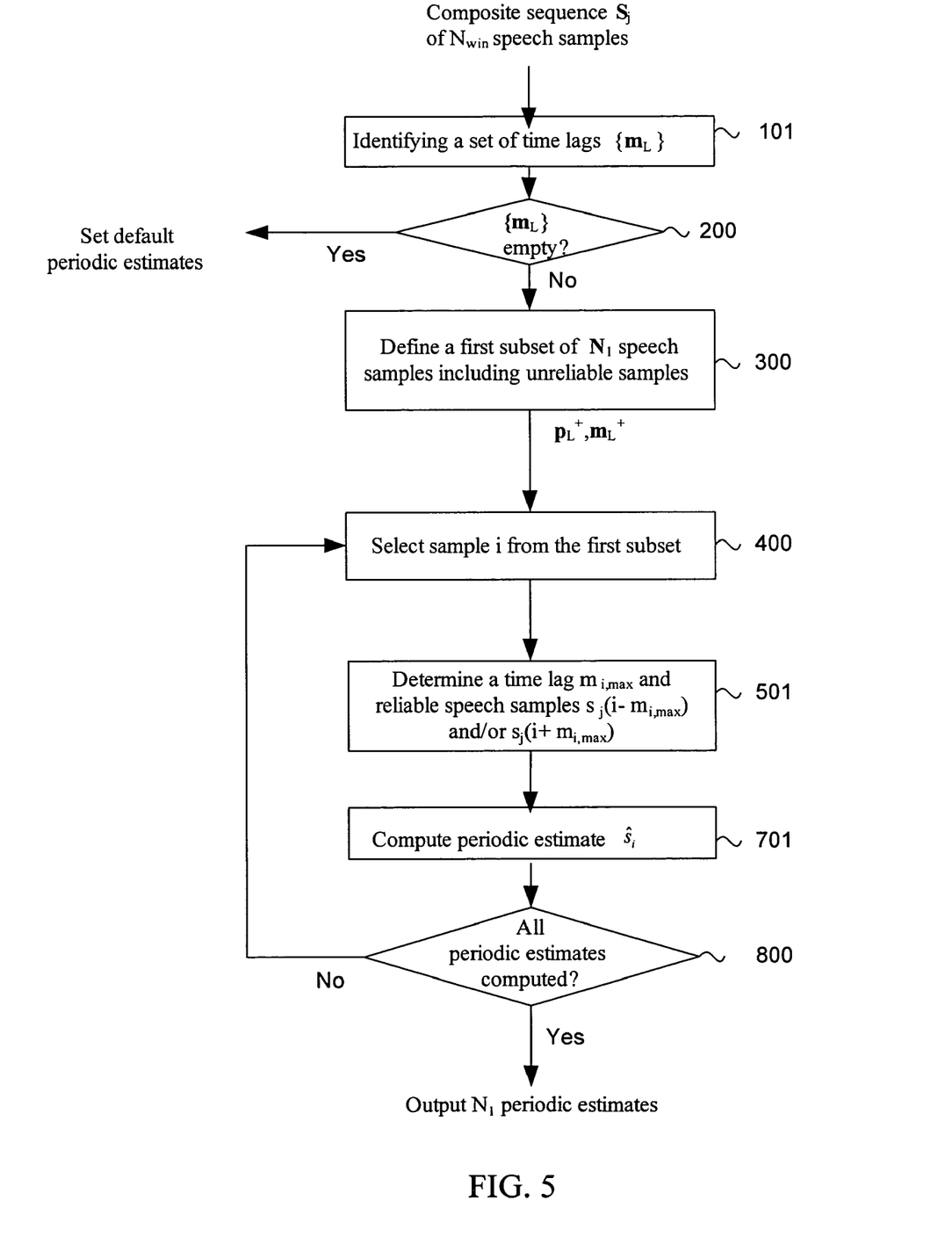
FIG. 5 is a diagram of a simplified method for generation of periodic estimates in accordance with instant invention.

With reference to FIG. 5, in another embodiment, the periodic estimates can be generated using a simplified method which retains the aforedescribed general scheme of the first exemplary embodiment, but drastically reduces complexity by computing a Wiener filter for the voiced component based on only a maximum correlation coefficient magnitude, implying the use of at most two lags per estimate, corresponding in the aforedescribed procedure L=1 and M=1 or 2. The simplified method retains most of the aforedescribed mains steps shown in FIG. 3, with the following modifications.

Figure 6:
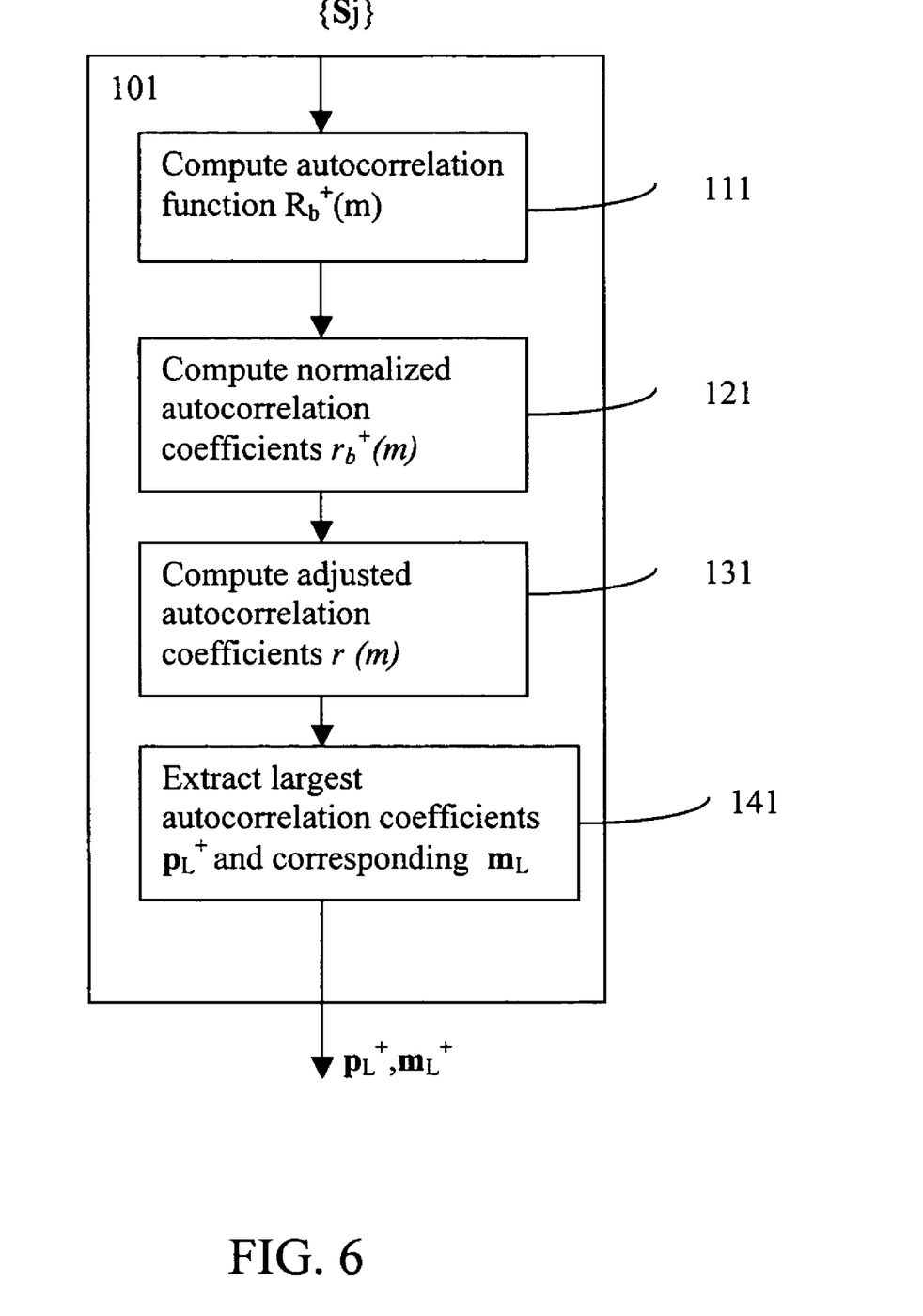
FIG. 6 is a diagram of a process of identifying a set of time lags for the method of FIG. 5.

With reference to FIG. 6, in a first step 111 the autocorrelation function is computed only for lags between $M_{min}$ and $M_{max}$:

$$R_b^+(m) = w(m) \cdot \sum_{l=|m|}^{N_{win}-|m|} s_j^*(l) \cdot s_j(l-m), m = M_{min}, \ldots, M_{max}. \quad (16)$$

This expression is identical to (1) except that less than half as many correlations are computed. After the aforedescribed normalization steps (3) and (4) and the adjustment procedure are performed, a set of $(M_{max} - M_{min})$ adjusted correlation coefficients $r(m)$ is obtained in step 131 similarly to step 130 shown in FIG. 4.

In step 141, vectors of largest correlation coefficients $p_L^+$ and of corresponding lags $m_L^+$ are then produced by, for example, comparing the coefficients with the threshold $T_{corr}$ as described in step 140 of the previous embodiment. If $p_L^+$ is empty, processing for the $j^{th}$ composite speech sequence is complete, and $N_{gap}$ corresponding periodic estimates for the unreliable samples are set to the default value. If $p_L^+$ is not empty, processing of samples from the first subset of samples starts, similarly to the aforedescribed embodiment, by selecting a sample index i from the first subset of samples. In a next step 501, a single time lag $m_{i,max}$ is selected from the set $m_L^+$ to satisfy two conditions:

a) at least one of speech samples $s(i - m_{i,max})$ and $s(i + m_{i,max})$ is a valid sample, and b) $|r(m_{i,max})|$ exceeds magnitudes of all other elements of the vector $p_L^+$ corresponding to lags m satisfying condition (a).

This can be accomplished, for example, by a following algorithm. First, local copies of vectors $m_L^+$ and $p_L^+$, namely $m'_L$ and $p'_L$, are crated. A correlation coefficient from $p'_L$ with a maximum magnitude and its associated lag are then found and tested to see whether or not they correspond to a reliable sample. If not, this maximum and its lag are deleted from $m'_L$ and $p'_L$ and the next maximum is found. This process is repeated until either a coefficient corresponding to a reliable sample is found or all of the lags that met threshold have been disqualified. In the latter case, processing for the current sample time is complete. In the former case, the vector $p'_L$ collapses to a single value, namely $r(m_{i,max})$. An interpolating FIR filter in this case has at most two tap coefficients, allowing for a simple computation of the periodic estimate $\hat{s}_i$. In fact, we found that sufficiently good results are obtained using a single tap coefficient $r(m_{i,max})$ for computation of the $i^{th}$ periodic estimate, as described by expression (17):

$$\hat{s}_i = r(m_{i,max}) \cdot s_i \quad (17)$$

If it is found that only one of the samples $s(i - m_{i,max})$ and $s(i + m_{i,max})$ is a reliable speech sample, vector $s_i$ is a single element vector computed as $$s_i = s_j(i - m_{i,max}). \quad (18)$$

Ignoring possible differences in the aforedescribed adjustment of the correlation function in the two embodiments, equations (17) and (18) are exactly what is yielded by the general method of the first exemplary embodiment if only one lag survives the test for available reliable samples.

If both samples $s_j(i - m_{i,max})$ and $s_j(i + m_{i,max})$ are reliable, the single-element vector $s_i$ can be computed as $$s_i = \frac{1}{2} \cdot [s_j(i + m_{i,max}) + s_j(i - m_{i,max})]. \quad (19)$$

In this case the filter is sub-optimal but yields significant computational savings, completely avoiding any issues surrounding matrix inversion by averaging the available samples and using the single autocorrelation coefficient $r(m_{i,max})$.

In some cases, outputting the periodic estimates computed for example using either one of the aforedescribed versions of the method of instant invention in place of the unreliable or lost speech samples can sufficiently improve perceived quality of the received speech signal. Therefore, in some embodiments the processing for lost speech samples can stop after generating the periodic estimates; in these embodiments, the first subset of speech samples may coincide with the sequence of unreliable speech samples, and the number Nov of overlap samples in the first and second overlap sets can be equal to 0.

However, in other cases adding estimates of the colored noise component to the periodic estimates for lost speech samples may enhance either version of the aforedescribed method for recovering of lost speech samples by generating periodic estimates. If the periodic estimates accurately represent the voice component of the composite speech sequence, then the differences between the known and interpolated samples in the overlap intervals may be modeled as a colored noise process. That is, a linear system whose transfer function approximates the spectral shape of the difference signal may be designed and used to shape a white noise process. Therefore, in the second aspect of the current invention a method of generation of colored noise estimates for lost speech samples is provided, wherein the colored noise estimates are determined by extrapolating a difference sequence of the received samples and their periodic estimates computed for the overlap sets of samples into the time slot of the lost samples. Since the noise-like component is non-periodic and unlikely to be continuous across any set of unreliable samples, one-sided linear prediction is used.

Generation of Coloured Noise Estimates

Figure 7:
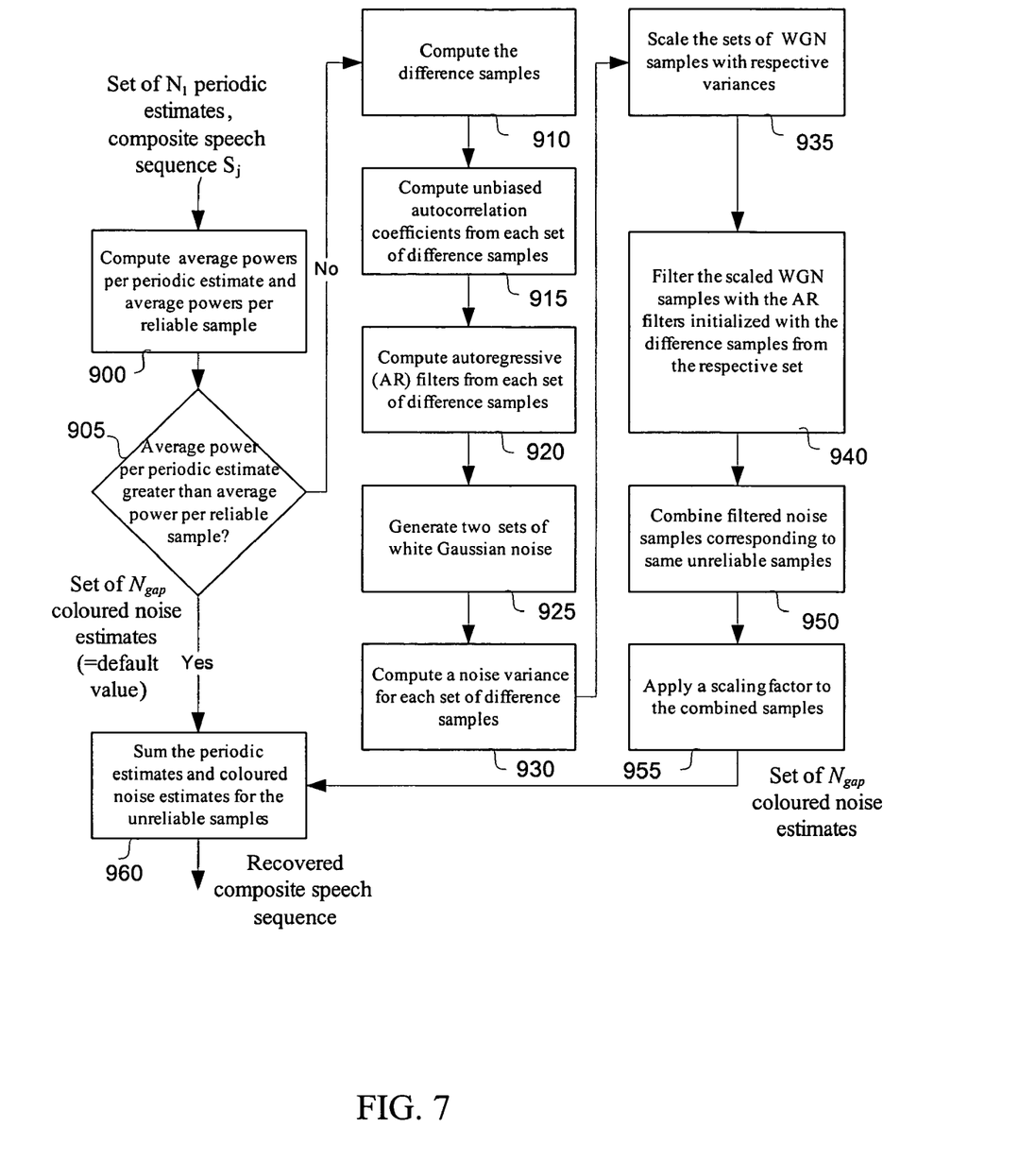
FIG. 7 is a diagram of a process of generation of colored noise estimates in accordance with instant invention.

With reference to FIG. 7, in a first step 900, an average power $P_T(j)$ per periodic estimate for the overlap intervals and an average power $P_{win}(j)$ per reliable sample for the $2 \cdot N_{est}$ reliable speech samples of the $j^{th}$ composite sequence of speech samples are computed, and compared to each other in a next step 905. If $P_T(j) \geq P_{win}(j)$, each colored noise estimate for the $N_{gap}$ unreliable samples is set to a global default value, and the processing for colored noise estimates stops.

If $P_T(j) < P_{win}(j)$, the processing continues by performing a next step 910 wherein two difference sequences $\Delta_{pre}$ and $\Delta_{post}$ for the first and second overlap sets respectively are calculated. The periodic estimates for the overlap intervals are subtracted from the corresponding reliable samples according to $$\Delta_{pre}(n) = s_j(n) - \hat{s}_P(n), n = N_{est} - N_{ov} - 1, \ldots, N_{est} - 1 \quad (20)$$

$$\Delta_{post}(n) = s_j(n) - \hat{s}_P(n), n = N_{est} + N_{gap} - 1, \ldots, N_{est} + N_{gap} + N_{ov} - 1 \quad (21)$$

where $\Delta_{pre}(n)$ is the set of difference samples preceding the gap hereafter referred to as a first set of difference samples, $\Delta_{post}(n)$ is the set of difference samples following the gap hereafter referred to as a second set of difference samples, and $s_j(n)$ is a speech sample from the $j^{th}$ composite sequence of received speech samples as before. These samples are then extrapolated into the time slot of the lost samples using a well-known method of linear predictions by autoregressive (AR) filtering as hereafter described. For convenience, both linear predictions can be described as forward predictions by time-reversing the $\Delta_{post}(n)$ vector to produce a time-reversed vector $\Delta'_{post}(n) = \Delta_{post}(N_{ov} - n)$.

In a next step 915, the vectors $\Delta_{pre}(n)$ and $\Delta'_{post}(n)$ are then respectively used to generate two autocorrelation functions $R_{pre}(m)$ and $R_{post}(m)$, $m = 0, \ldots, p$, and two distinct sets of $p+1$ unbiased autocorrelation coefficients $r_{pre}(m)$ and $r_{post}(m)$, in much the same way as described herein with reference to expressions (1) and (4). These autocorrelation coefficients in a next step 920 are used to solve a system of Yule-Walker equations, wherefrom parameters of two $p^{th}$ order AR models of processes that produced the difference samples $\Delta_{pre}(n)$ and $\Delta'_{post}(n)$ are found. Details of the AR approach which is well known to those skilled of the art and can be found for example in a book by J. G. Proakis and D. G. Manolakis, entitled "Digital Signal Processing: Principles, Algorithms, and Applications", Prentice Hall, $3^{rd}$ Edition, 1996.

Both filters are then tested for stability by examining their reflection coefficients. Details of this process of testing filter stability are well known to those skilled in the art, can be found for example in Proakis et al., 1996, and are not described herein. If one or more reflection coefficients for one of the filters is greater than or equal to one, the filter is unstable, and p is reduced by one and the filter design process repeated by formulating a solving a new set of Yule-Walker equations, until stability is achieved. The resulting two filters $h_{pre}$ and $h_{post}$, which are defined by their corresponding sets of AR tap coefficients $\{\alpha_{m,pre}\}$, $m = 0 \ldots p_{pre} - 1$, and $\{\alpha_{m,post}\}$, $m = 1 \ldots p_{post} - 1$, may therefore be of different lengths, having $p_{pre}$ and $p_{post}$ nonzero tap coefficients respectively.

In a following step 925, two noise sequences are generated each containing $N_{gap}$ samples of white Gaussian noise (WGN). Next, in a step 930, two scaling factors $k_{pre} = \sigma_{N,pre}$ and $k_{post} = \sigma_{N,post}$ for scaling the generated WGN samples are computed from appropriate variances $\sigma^2_{N,pre}$ and $\sigma^2_{N,post}$ for the two WGN sequences respectively from expressions (22) and (23):

$$\sigma^2_{N,pre} = \sum_{m=0}^{p_{pre}} a_{m,pre} \cdot R_{pre}(m) \quad (22)$$

$$\sigma^2_{N,post} = \sum_{m=0}^{p_{post}} a_{m,post} \cdot R_{post}(m) \quad (23)$$

where $R_{pre}(m)$ and $R_{post}(m)$ are the unbiased autocorrelation functions, not to be confused with correlation coefficients, and the $\alpha_{m,pre}$ and $\alpha_{m,post}$ are the sets of AR filter coefficients. In a next step 935, the two noise sequences are scaled with the corresponding scaling coefficients $k_{pre}$ and $k_{post}$ to produce two scaled noise sequences.

In a next steps 940, each of the two all-pole AR filters are initialized with respectively $p_{pre}$ and $p_{post}$ difference samples from respectively the first and second sets of difference samples, the $p_{pre}$ and $p_{post}$ valid speech samples being immediately adjacent to the gap, and then excited with the $N_{gap}$ scaled WGN samples. The initialization with previous outputs of a desired process ensures a smooth transition from known samples to predicted samples at the gap edges, removing discontinuities that might produce audible degradation in voice quality, and eliminates any concerns about filter transients. As a result, two sets of $N_{gap}$ colored noise estimates are produced forming two estimate vectors $\hat{c}_{N,pre}(i)$ and $\hat{c}'_{N,post}(i)$, $i = 0, \ldots, N_{gap} - 1$.

The aforedescribed AR filtering operation producing $\hat{c}_{N,pre}(i)$ is expressed by an equation $$\hat{c}_{N,pre}(i) = \sum_{m=0}^{p_{pre}} a_{m,pre} \cdot \hat{c}_{N,pre}(i-m) + v_{pre}(i) \quad (24)$$

where $v_{pre}(i)$ is a WGN sample from one of the scaled noise sequences, and first $p_{pre}$ noise estimates $\hat{c}_{N,pre}(i-m)$, $m = 1 \ldots p_{pre}$, corresponding to a first unreliable symbol position $i = N_{est}$ closest to the first sequence 7 of the valid samples, are the $p_{pre}$ difference samples from the first set of difference samples defined by expression (20) that are immediately adjacent to the sequence of unreliable samples 2:

$$\hat{c}_{N,pre}(N_{est} - m) = \Delta_{pre}(N_{est} - m), m = 1 \ldots p_{pre}.$$

An expression similar to expression (24) holds for $\hat{c}'_{N,post}(i)$.

In a next step 950 the two estimate vectors are then each scaled, and elements of the scaled estimate vectors summed together to produce a noise-like vector $\hat{c}_N(i)$ having Ngap elements.

Many different scaling functions are possible; a good choice is a quarter cycle of a sinusoid matched to the gap duration, namely $$w_N(i) = \cos\left(\frac{\pi}{2} \cdot \frac{i}{N_{gap}}\right), i = 0, \ldots, N_{gap} - 1 \quad (25)$$

The noise-like vector $\hat{c}_N(i)$ is computed by adding the two sets of estimates where those corresponding to the end of the gap are again time-reversed, i.e. it is computed as $$\hat{c}'_N(i) = w_N(i) \cdot \hat{c}_{N,pre}(i) + w_N(N_{gap} - i) \cdot \hat{c}'_{N,post}(N_{gap} - i) \quad (26)$$

$$= \cos\left(\frac{\pi}{2} \cdot \frac{i}{N_{gap}}\right) \cdot \hat{c}_{N,pre}(i) +$$

$$\sin\left(\frac{\pi}{2} \cdot \frac{i}{N_{gap}}\right) \cdot \hat{c}'_{N,post}(i)(N_{gap} - i), i = 0, \ldots, N_{gap} - 1.$$

With this choice of the scaling functions, the estimates adjacent to the preceding gap edge are almost exclusively a function of the predicted samples computed from that edge and vice versa. At the centre of the gap, contributions from both edges are weighted equally. The overall scaling function has unit power.

In a final step 960 of computation of the colored noise estimates, the vector $\hat{c}'_N(i)$ is scaled again with a power scaling factor representing a normalized power difference of the periodic estimates and the reliable samples to produce a vector $\hat{s}_N(i)$ of the colored noise estimates for the $N_{gap}$ unreliable speech samples:

$$\hat{s}_N(i) = \frac{\hat{c}'_N(i)}{2} \cdot \left(1 - \frac{P_T(j)}{P_{win}(j)}\right), i = 0, \ldots, N_{gap} - 1 \quad (26)$$

Finally, estimates for the unreliable speech samples are computed by adding together the periodic estimates and the colored noise estimates for each unreliable speech sample position, and a recovered composite sequence of speech samples is produced by substituting the computed estimates for the unreliable speech samples in the received composite sequence of speech samples.

In a system for recovering lost or unreliable speech samples in a speech transmission system, the method disclosed herein would be invoked by a suitably programmed processor capable of executing the method steps described herein, having sufficient memory for storing relevant speech and processing data, and programmed with a computer code for executing the method steps described herein.

Of course numerous other embodiments may be envisioned without departing from the spirit and scope of the invention, and numerous changes and modifications as known to those skilled in the art could be made to the present invention. For example, reference has been made to the reception of speech information in the present invention, however, the present invention is not limited to voice or speech information. The present invention may be used for any real-time sound transmission over a transmission system, including an IP network and a wireless communication systems. Further, the present invention may be used to receive sound data in conjunction with video data. Therefore, the invention is not limited to the details shown and described herein, but intend to cover all such changes and modifications as are encompassed by the scope of the appended claims.

What is claimed is:

1. A method for recovering lost or unreliable speech samples in a speech transmission system, comprising the steps of:
   (a) receiving a composite sequence of speech samples which includes a sequence of unreliable speech samples and a sequence of reliable speech samples, each speech sample having a value and a position in the composite speech sequence, the composite sequence of speech samples having a pitch period $T_p$ having a value between a minimum value $T_{min}$ and a maximum value $T_{max}$;
   (b) identifying a set of time lags from correlations between at least some of the reliable speech samples;
   (c) for a speech sample from a first subset of speech samples from the composite sequence of speech samples, the first subset of speech samples including unreliable speech samples from the sequence of unreliable speech samples, selecting a set of reliable speech samples wherein each reliable speech sample is offset from the speech sample by a time lag from the set of time lags;
   (d) computing a periodic estimate for the speech sample from the first subset of speech samples using the set of reliable speech samples and using an adaptive FIR interpolation filter, wherein the adaptive FIR interpolation filter is dependent on a position of the speech sample from the first subset of speech samples;
   (e) repeating steps (c) and (d) for each speech sample from the first subset of speech samples so as to obtain periodic estimates for the unreliable speech samples;
   (f) producing a recovered sequence of speech samples utilizing the periodic estimates for each unreliable speech sample;
   wherein step (c) comprises selecting the set of reliable speech samples to include speech samples from a first sequence of reliable speech samples preceding the sequence of unreliable speech samples, and a second sequence of reliable speech samples following the sequence of unreliable speech samples, so that step (d) comprises computing the periodic estimate for the speech sample based on at least one reliable speech sample preceding said speech sample and at least one reliable speech sample following said speech sample;
   wherein the FIR interpolation filter has tap coefficients determined from correlations between at least some of the reliable speech symbols;
   wherein the step of identifying the set of time lags between $T_{min}$ and $T_{max}$ from correlations between reliable speech samples comprises the steps of:
   computing a set of autocorrelation coefficients for the sequence of reliable speech samples for a sequence of time lags,
   identifying a subset of largest autocorrelation coefficients from the set of correlation coefficients corresponding to time lags between $T_{min}$ and $T_{max}$;
   identifying a set of time lags corresponding to the subset of largest autocorrelation coefficients; and,
   wherein the step of selecting a set of reliable speech samples for a speech sample from the first subset of speech samples comprises the steps of: from time offsets between the speech sample and the set of reliable speech samples, identifying a local subset of M time lags of the set of time lags, and identifying a local subset of autocorrelation coefficients corresponding to the local subset of M time lags.

2. A method of claim 1 wherein the subset of largest autocorrelation coefficients is determined using a pre-defined correlation threshold.

3. A method of claim 1 wherein the subset of largest autocorrelation coefficients is a subset of L largest autocorrelation coefficients from the set of autocorrelation coefficients, wherein L is a pre-determined integer number.

4. A method as defined in claim 3, wherein L=1 and M=1.

5. A method as defined in claim 4, wherein the local subset of reliable speech samples consists of one sample "s", and wherein the step of computing comprises a step of multiplying the sample "s" by an autocorrelation coefficient corresponding to a time lag L equal to a time offset between the speech sample from the first subset of speech samples and the reliable sample "s".

6. A method as defined in claim 4, wherein the local subset of reliable speech samples consists of two samples "$s^+$" and "$s^-$" offset from the speech sample from the first subset of speech samples by time lags +L and −L respectively, and wherein the step of computing comprises a step of multiplying a mean value of the samples "$s^+$" and "$s^-$" by a correlation coefficient corresponding to the time lag L.

7. A method as defined in claim 1, wherein the subset of largest autocorrelation coefficients is augmented to include correlation coefficients corresponding to negative time lags.

8. A method as defined in claim 1, wherein the first subset of speech samples comprises an overlap set of reliable speech samples adjacent to the sequence of unreliable speech samples, so that step (e) comprises computing periodic estimates for the overlap set of reliable speech samples.

9. A method as defined in claim 8, farther comprising the step of calculating a set of difference samples by subtracting the periodic estimates from the corresponding speech samples from the overlap set.

10. A method as defined in claim 8, further comprising a step of, for the overlap set of speech samples, comparing an average power per sample for the reliable speech samples and an average power per sample for the periodic estimates for determining a power scaling factor.

11. A method as defined in claim 9, farther comprising the steps of
for each unreliable speech sample from the first subset of speech samples,
a) computing an estimate of a colored noise component by extrapolating the set of difference samples to the unreliable speech sample position, and
b) combining the periodic estimate of the unreliable speech sample and the estimate of the colored noise component for determining an estimate of a value of the unreliable speech sample.

12. A method as defined in claim 11, wherein the step of computing an estimate of a colored noise component by extrapolating the noise component to the unreliable speech sample position includes the step of autoregressive filtering of randomly generated noise samples.

13. A method as defined in claim 12, wherein the step of autoregressive filtering includes the step of computing a first noise estimate for the unreliable speech sample from the first set of difference samples by performing the steps of:
computing a set of autocorrelation coefficients from the first set of difference samples;
determining tap coefficients of a first autoregressive filter from the set of autocorrelation coefficients;
initializing the first autoregressive filter, defined in part by the tap coefficients, with samples from the first set of difference samples;
generating a noise sample;
scaling the noise sample with the power scaling factor; and,
applying the first autoregressive filter to the noise sample for producing a noise estimate for the unreliable speech sample.

14. A method as defined in claim 12, wherein the overlap set includes a first overlap set preceding the sequence of the unreliable speech samples, and wherein the set of difference samples includes a first set of difference samples calculated from the first overlap set.

15. A method as defined in claim 14, wherein the overlap set includes a second overlap set following the sequence of the unreliable speech samples, and wherein the set of difference samples includes a second set of difference samples calculated from the second overlap set.

16. A method as defined in claim 15, wherein the step of autoregressive filtering includes the step of computing a second noise estimate for the unreliable speech sample from the second set of difference samples.

17. A method as defined in claim 16, wherein the step of computing a noise estimate for an unreliable speech sample includes the steps of:
scaling of the first and second noise estimates for producing a first scaled noise estimate and a second scaled noise estimate; and,
combining the first and second scaled noise estimates for providing the noise estimate for the unreliable speech sample.

18. A method for recovering lost or unreliable speech samples in a speech transmission system, comprising the steps of:
(a) receiving a composite sequence of speech samples which includes a sequence of unreliable speech samples and a sequence of reliable speech samples, each speech sample having a value and a position in the composite speech sequence, the composite sequence of speech samples having a pitch period $T_p$ having a value between a minimum value $T_{min}$ and a maximum value $T_{max}$;
(b) identifying a set of time lags from correlations between at least some of the reliable speech samples;
(c) for a speech sample from a first subset of speech samples from the composite sequence of speech samples, the first subset of speech samples including unreliable speech samples from the sequence of unreliable speech samples, selecting a set of reliable speech samples wherein each reliable speech sample is offset from the speech sample by a time lag from the set of time lags;
(d) computing a periodic estimate for the speech sample from the first subset of speech samples using the set of reliable speech samples and using an adaptive FIR interpolation filter, wherein the adaptive FIR interpolation filter is dependent on a position of the speech sample from the first subset of speech samples;
(e) repeating steps (c) and (d) for each speech sample from the first subset of speech samples so as to obtain periodic estimates for the unreliable speech samples;
(f) producing a recovered sequence of speech samples utilizing the periodic estimates for each unreliable speech sample;
wherein step (c) comprises selecting the set of reliable speech samples to include speech samples from a first sequence of reliable speech samples preceding the sequence of unreliable speech samples, and a second sequence of reliable speech samples following the sequence of unreliable speech samples, so that step (d) comprises computing the periodic estimate for the speech sample based on at least one reliable speech sample preceding said speech sample and at least one reliable speech sample following said speech sample;

wherein the FIR interpolation filter has tap coefficients determined from correlations between at least some of the reliable speech symbols;

wherein the tap coefficients of the FIR interpolation filter are determined by performing the steps of:

constructing an M×M autocorrelation matrix from a set of correlation coefficients corresponding to differences between time lags from the local subset of M time lags;

inverting the autocorrelation matrix to obtain an inverted autocorrelation matrix; and, multiplying the inverted autocorrelation matrix by a vector formed from the local subset of correlation coefficients for obtaining a vector of the tap coefficients.

19. A method as defined in claim 18, wherein the step of computing the periodic estimate for the speech sample from the first subset of speech samples includes the step of summing results of element-by-element multiplication of the vector of tap coefficients and a vector formed from the set of reliable speech samples.

* * * * *